United States Patent
Mamayek (10) Patent No.: US 6,358,211 B1
(45) Date of Patent: Mar. 19, 2002

(54) ULTRASOUND LUCENT APPARATUS AND METHODS OF USING

(75) Inventor: Donald S. Mamayek, Mountain View, CA (US)

(73) Assignee: Scimed Life Systems, Inc., Maple Grove, MN (US)

(*) Notice: Subject to any disclaimer, the term of this patent is extended or adjusted under 35 U.S.C. 154(b) by 0 days.

(21) Appl. No.: 09/416,125

(22) Filed: Oct. 12, 1999

(51) Int. Cl.[7] ................................. A61B 8/14
(52) U.S. Cl. ................... 600/459; 600/462; 600/466
(58) Field of Search ................... 600/407, 424, 600/431–435, 437, 439, 443–447, 459–472, 585, 438; 607/122

(56) References Cited

U.S. PATENT DOCUMENTS

| | | |
|---|---|---|
| 3,802,759 A | 4/1974 | Andersson |
| 4,356,880 A | 11/1982 | Downs |
| 4,551,726 A | 11/1985 | Berg |
| 4,794,931 A | 1/1989 | Yock |
| 4,990,918 A | 2/1991 | Michelson et al. |
| 5,095,911 A | 3/1992 | Pomeranz |
| 5,108,411 A | 4/1992 | McKenzie |
| 5,203,338 A | 4/1993 | Jang |
| 5,348,017 A | 9/1994 | Thornton et al. |
| 5,437,282 A | 8/1995 | Koger et al. |
| 5,490,521 A | 2/1996 | Davis et al. |
| 5,503,155 A | 4/1996 | Salmon et al. |
| 5,544,660 A | 8/1996 | Crowley |
| 5,549,108 A | 8/1996 | Edwards et al. |
| 5,620,417 A | 4/1997 | Jang et al. |
| 5,759,154 A | 6/1998 | Hoyns |
| 5,908,445 A * | 6/1999 | Whayne et al. ............ 607/122 |
| 5,921,933 A | 7/1999 | Sarkis et al. |
| 6,193,676 B1 * | 2/2001 | Winston et al. ............ 600/585 |

FOREIGN PATENT DOCUMENTS

| | | | |
|---|---|---|---|
| EP | 0 386 936 A1 | 9/1990 | ........... A61B/8/08 |
| FR | 2 272 633 | 12/1975 | |
| JP | 56 004006 | 1/1981 | |

OTHER PUBLICATIONS

Martin, Roy W. and Johnson, Christopher C.; Design characteristics for intravascular ultrasonic catheters, *International Journal of Cardiac Imaging*, 1989, vol. 4, pp. 201–216.

* cited by examiner

*Primary Examiner*—Marvin M. Lateef
*Assistant Examiner*—Ali M. Imam
(74) *Attorney, Agent, or Firm*—Townsend and Townsend and Crew, LLP (57) ABSTRACT

The present invention provides exemplary ultrasound lucent apparatus and methods for use in a wide range of invasive imaging and surgical procedures. In one exemplary embodiment, an apparatus (10) comprises an elongate wire body (12) having an outer surface and a longitudinal axis (18). The wire body includes a plurality of corner reflectors (22) disposed on an embossed portion (20) of the outer surface. The wire body is adapted to be inserted into a body lumen or a patient vasculature. In this manner, use of corner reflector technology enhances the ultrasound reflective nature to increase the acoustical reflectivity of the wire body.

29 Claims, 7 Drawing Sheets

ULTRASOUND LUCENT APPARATUS AND METHODS OF USING

BACKGROUND OF THE INVENTION

The present invention relates generally to ultrasonic imaging systems, and more particularly, to ultrasound lucent apparatus for use with such imaging systems.

Intravascular imaging of blood vessels and surrounding tissues continues to be of great benefit in a wide range of medical fields. In some configurations, a flexible guidewire is inserted into a patient, for example, through the femoral artery, and positioned at a desired location within the patient. An imaging catheter is then inserted into the patient and positioned at the desired location within the patient. In some embodiments, the imaging catheter is disposed in a sheath having an opening or hole at the distal end and an opening or hole in the sheath wall a number of inches from the distal tip. The imaging catheter is then guided "over the wire" and positioned at the desired location.

For the above-described embodiment as well as other medical procedures, including less invasive surgical procedures (LISA), it is desirable to precisely locate the guidewire distal tip or guidewire body. Locating the distal tip, for example, typically is not a trivial exercise in light of the small dimensions and generally cylindrical shape of the guidewire. For example, ultrasound imaging techniques used from outside the patient's body may have difficulty in locating a diminutive, round guidewire. It is preferable to provide a guidewire for use with imaging systems that provide for greater ease of location and recognition. However, increasing the size of the guidewire is not desirable, particularly in light of the narrow and tortuous vasculature of the patients in many locations being treated.

SUMMARY OF THE INVENTION

The present invention provides exemplary ultrasound lucent apparatus and methods for use in a wide range of imaging and surgical procedures. At least part of the present invention is directed to providing a guidewire having a greater reflectivity to increase the likelihood the guidewire will be located and correctly positioned. In one exemplary embodiment of the present invention, an apparatus to aid ultrasound imaging or treatment of a patient comprises an elongate wire body having an outer surface and a longitudinal axis. The wire body includes a plurality of corner reflectors disposed on an embossed portion of the outer surface. The wire body is adapted to be inserted into a body lumen or a patient vasculature. In this manner, use of corner reflector technology enhances the ultrasound reflective nature to increase the acoustical reflectivity of the wire body.

In one aspect of the present invention, the embossed portion is positioned to be generally coaxial with the longitudinal axis and extends around a portion of the circumference of the wire body. Alternatively, the embossed portion includes a band around the entire circumference of the wire body.

To facilitate introduction into a patient, the wire body preferably has a diameter that is less than about 20 French. The wire body comprises a stainless steel, or tungsten in two alternative embodiments.

In one aspect, the plurality of corner reflectors each comprise first, second and third sides, with each side having a generally triangular shape and positioned to be generally orthogonal to the other two sides, such as an inside corner of a box. In one aspect, each of the three sides have an isosceles triangle shape. Alternatively, each of the three sides have a right triangle shape and share a common vertex.

In one particular aspect, the apparatus further includes a sleeve with the wire body disposed therein. Preferably, the sleeve comprises a material selected from a group of materials consisting of a plastic, a metalized plastic, a metal, a plastic-coated metal, two or more plastics of different density, and the like. In this manner, the sleeve facilitates smooth introduction of the apparatus into a patient and comprises material permissible for use within the patient.

In one aspect, the apparatus further includes a second embossed portion of the wire body, having a second plurality of corner reflectors. In another aspect, the wire body is a wound wire body. The wire body comprises a plurality of windings around the body longitudinal axis.

In one particular aspect, an ultrasound lucent wire is provided having a wound wire body. The wire body has a flexible distal end, a proximal end, a longitudinal axis. and an outer surface. The wire body includes a plurality of corner reflectors embossed in the outer surface to define an embossed portion thereof. The wire body has a diameter that is less than about 20 French.

In another embodiment, an apparatus to aid ultrasound imaging or treatment of a patient includes a hollow sleeve having an inner surface and an outer surface and a flexible wire disposed in the sleeve. At least a portion of the wire is embossed with a plurality of corner reflectors to enhance ultrasound visibility of the apparatus.

In one particular embodiment, an apparatus to aid ultrasound imaging or treatment of a patient includes a hollow sleeve having inner and outer surfaces, and a flexible wire disposed in the sleeve. The sleeve has a first portion embossed with a plurality of corner reflectors. In this manner, the corner reflectors for increasing ultrasound visibility of the apparatus are disposed on or in the sleeve.

In one aspect, the first sleeve portion embossed with the plurality of corner reflectors includes a portion of the inner surface of the sleeve. Alternatively, the corner reflectors are disposed on a portion of the outer surface of the sleeve. In one aspect, the sleeve includes a sleeve material having a sleeve material density. The first sleeve portion embossed with the corner reflectors is coated with a material having a greater density than the sleeve material density.

In one aspect, the sleeve, or the wire body, or both, includes a second embossed portion having corner reflectors. In still another aspect, the sleeve is disposed within a second sleeve.

The present invention further provides exemplary methods of performing an invasive medical procedure, such as an imaging or surgical procedure. In one method, a guide wire is provided having a wire body with a plurality of corner reflectors embossed in the guidewire body outer surface. The method includes inserting the guidewire into a patient, and positioning the guidewire at a desired location within the patient. The method includes energizing a transducer to project an ultrasound signal in the general direction of the embossed portion, and capturing a reflected signal from the embossed portion. The method includes rotating the guide wire so that the embossed portion faces away from the transducer to reduce the reflected signal. In one aspect, an ultrasound imaging catheter having the transducer also is inserted into the patient.

Other features and advantages of the invention will appear from the following description in which the preferred embodiment has been set forth in detail in conjunction with the accompanying drawings.

DETAILED DESCRIPTION OF THE SPECIFIC EMBODIMENTS

Figure 1:
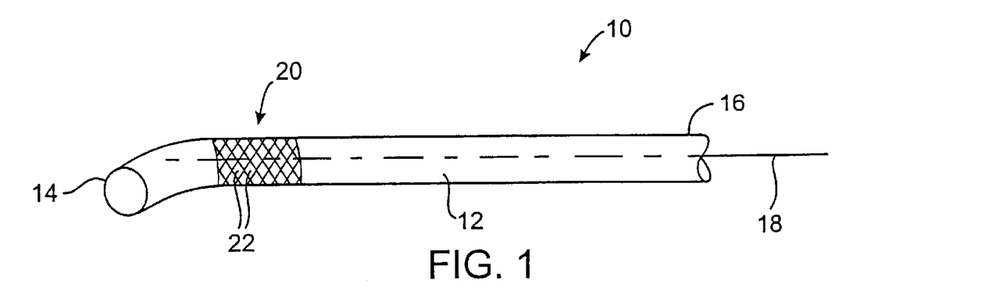
FIG. 1 depicts an overall view of an ultrasound lucent guidewire of the present invention.

FIG. 1 depicts an ultrasound imaging enhancement apparatus 10. Apparatus 10 comprises a wire body 12 having a distal end 14, a proximal end 16, and a longitudinal axis 18. Preferably, wire body 12 is less than about 20 French to facilitate introduction thereof into a patient vasculature. Wire body 12, in one embodiment, has a length that is about one to three meters. It will be appreciated by those skilled in the art that a larger, smaller, longer or shorter apparatus 10 may be used within the scope of the present invention. In some embodiments, wire body 12 comprises a stainless steel, tungsten, stainless steel coated with tungsten, and the like. In other embodiments, wire body 12 comprises a plastic or virtually any material compatible with the introduction of wire body 12 into a human patient. In one particular embodiment, distal end 14 has a slight curvature to it. In this manner, wire body 12 can be positioned to travel down a desired vein or artery by positioning distal end 14 to enter that artery or vein.

Apparatus 10 includes an embossed portion 20 having a plurality of corner reflectors 22 around at least a part of the circumference of wire body 12. Use of the term embossed is not intended to limit the manner in which plurality of corner reflectors 22 are disposed on wire body 12. For example, embossed portion 20 containing corner reflectors 22 may be formed via impression, molding, embossing, and a variety of other mechanisms.

For example, embossing of reflectors 22 can be accomplished by chemical etching using a photo mask and processing, by laser machining using a photo mask or direct write, by ion milling using a mask and processing, or by a three dimensional masking technique, among others.

Figure 2A:
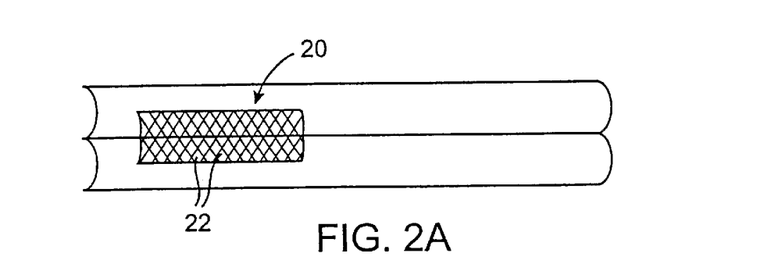
FIGS. 2A–2C depict split overall views of alternative configurations of the embossed portion of the lucent wires shown in FIG. 1.
Figure 2B:
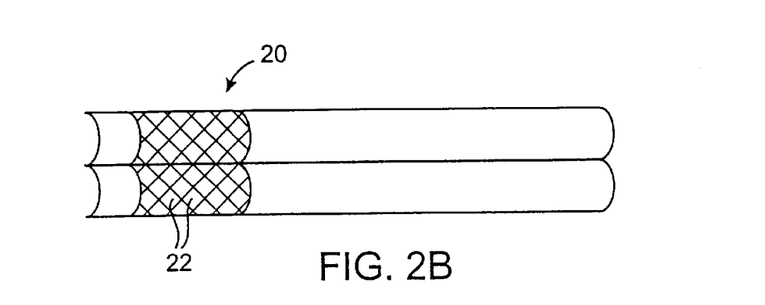
Figure 2C:
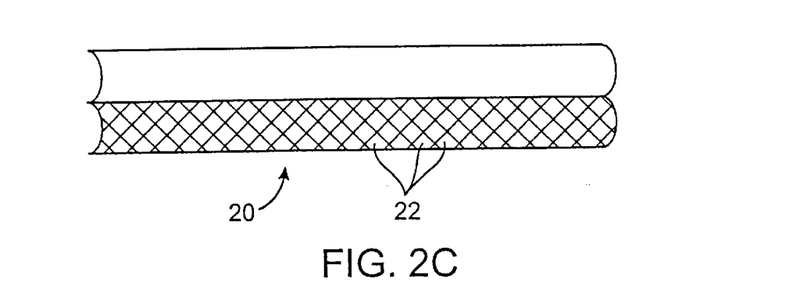

FIGS. 2A–2C depict alternative embodiments of apparatus 10 described in FIG. 1. In FIG. 2A, embossed portion 20 is generally coaxial with longitudinal axis 18 and extends part way, but not the entire way, around a circumference of wire body 12. In contrast, the embodiment depicted in FIG. 2B depicts a band shaped embossed portion 20 having plurality of corner reflectors 22 disposed around the complete circumference of wire body 12 in a defined area. Similarly, in another embodiment, FIG. 2C depicts embossed portion 20 having plurality of corner reflectors 22 positioned around approximately one half of the circumference of wire body 12 and extending in the axial direction a greater length than the embodiments depicted in FIGS. 2A or 2B. It will be appreciated by those skilled in the art that a number of other configurations of embossed portion 20 may be used within the scope of the present invention. While wire body 12 is depicted in FIGS. 2A–2C as having a generally circular cross-section, other shaped bodies 12 are used in other embodiments. Wire body 12, for example, may be round, flattened round (i.e., oval or "D" shaped), flat, and the like, with corner reflectors 22 embossed or otherwise included on or in the surface thereof.

Figure 3A:
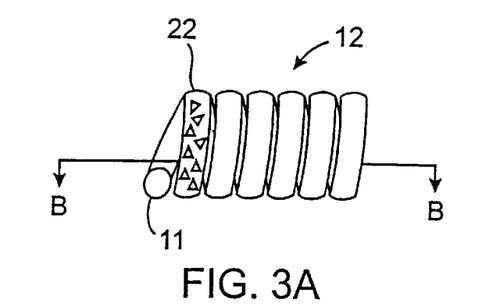
FIGS. 3A, 3C and 3E depict alternative embodiments of apparatus of the present invention.
Figure 3B:
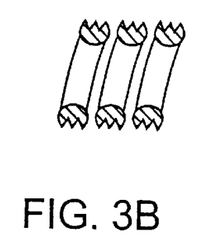
FIGS. 3B, 3D and 3F are cross-sectional views of the embodiments depicted in FIGS. 3A, 3C and 3E, respectively.
Figure 3C:
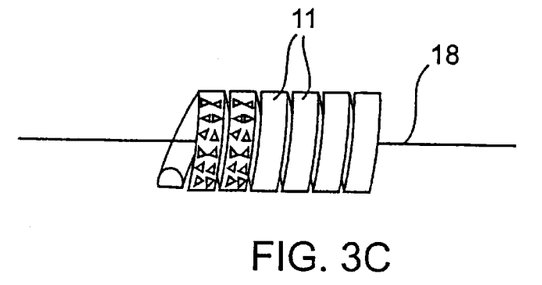
Figure 3D:
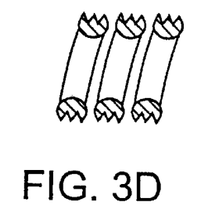
Figure 3E:
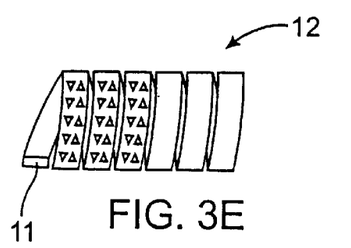
Figure 3F:
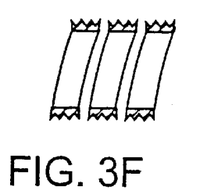

Turning now to FIGS. 3A–3F, additional embodiments of the present invention will be described. FIGS. 3A, 3C and 3E are side views of a wound wire 11 that is wound to define wire body 12. FIGS. 3B, 3D and 3F are cross sectional views of the apparatus of FIGS. 3A, 3C and 3E, respectively. The embodiment in FIGS. 3A–3B uses wire 11 having a generally circular cross section. The embodiment in FIGS. 3C–3D uses wire 11 having a generally oval or D-shaped cross section. The embodiment in FIGS. 3E–3F uses wire 11 having a generally flat or rectangular cross section.

In these embodiments, wire body 12 is defined by a plurality of windings of wire 11 around longitudinal axis 18. The formation of wire body 12 with a plurality of windings produces a flexible wire body 12 to facilitate the introduction of the apparatus into tortuous vasculatures or other body lumens. As shown, corner reflectors 22 preferably are disposed on an outward-facing surface of wire body 12. This can be accomplished, for example, by having corner reflectors 22 embossed on one side of the wound wire 11, and then winding the wire so that the embossed side is the outward-facing side. It will be appreciated by those skilled in the art that the corner reflector patterns shown in FIGS. 2A–2C also can be achieved for embodiments using wound wire 11 defining wire body 12. For example several spaced apart embossed sections can be formed on one side of wound wire 11, such that after wire 11 is wound, the embossed sections are generally aligned on one outward facing side of wire body 12 as in FIG. 2C.

Figure 4A:
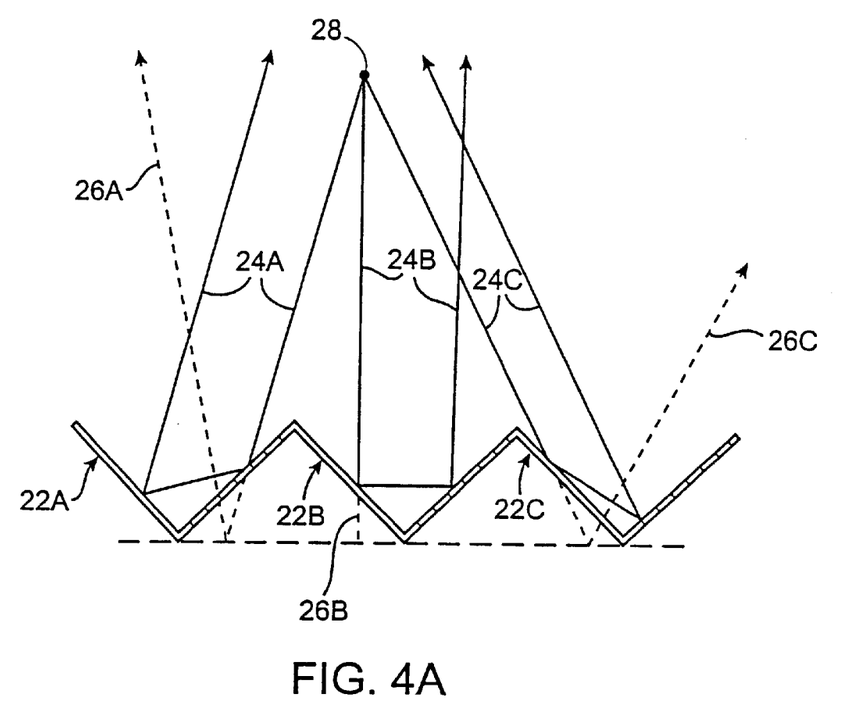
FIG. 4A depicts a two-dimensional diagram illustrating the soundwave reflected patterns from a series of corner reflectors according to the present invention.

Corner reflectors make use of the general principal that the angle of incidence of an ultrasound or other energy wave upon a reflective surface, measured relative to the surface normal, is generally the same for the incident ray and the reflected ray. Corner reflectors are described in conjunction with the two dimensional depiction shown in FIG. 4A. FIG. 4A is used for illustrative purposes and is not intended to limit the scope of the present invention. For example, corner reflectors of the present invention do not need to be connected together to perform in unison as depicted in FIG. 4A, nor are they required to be specifically focused. Further, FIG. 4A reveals a two-dimensional depiction, while in practice corner reflectors are three dimensional.

FIG. 4A depicts a source 28, such as an ultrasound transducer, which generates ultrasound waves in a manner known to those skilled in the art. Source 28 is positioned some distance from three corner reflectors 22A, 22B and 22C. Source 28 propagates ultrasound signals in the general direction of corner reflectors 22A–22C as indicated by rays 24A, 24B and 24C. Rays 24A–24C strike corner reflectors 22A–22C and reflect back toward source 28 as indicated.

For example, ray 24A reflects off corner reflector 22A resulting in the reflection of an ultrasound signal back in the general direction of source 28. In similar fashion, rays 24B and 24C reflect off of corner reflectors 22B and 22C, respectively, and return in the direction of source 28.

Dashed lines in FIG. 4 depict the reflection of rays 24A–24C off of a flat surface shown as another dashed line connecting the vertices of the three corner reflectors. Absent corner reflectors 22A–22C, rays 24A–24C do not provide as strong a return signal towards source 28 as occurs with corner reflectors 22. When a number of corner reflectors 22 according to the present invention are placed about source 28, each contributes its own reflected ultrasound signal to the vicinity of the source.

Figure 4B:
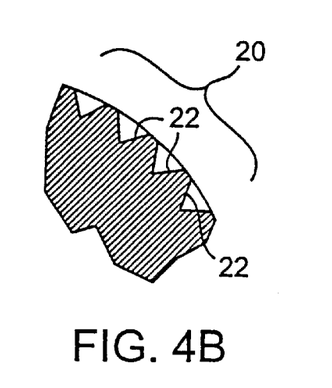
FIG. 4B depicts a cross section of a portion of an ultrasound lucent wire according to the present invention.

The strength of a return signal is further diminished when reflecting off of a convex curved surface. A curved wire surface presents a smaller profile to reflect ultrasound waves towards source 28 than the flat surface of FIG. 4A. The use of corner reflectors 22 on a guidewire improves the wire image profile, and hence, the return signal strength. FIG. 4B depicts a partial cross-sectional view of apparatus 10 showing plurality of corner reflectors 22 making up embossed section 20. Corner reflectors 22 operate to increase the strength of the reflected signal from embossed section 20.

Figure 5A:
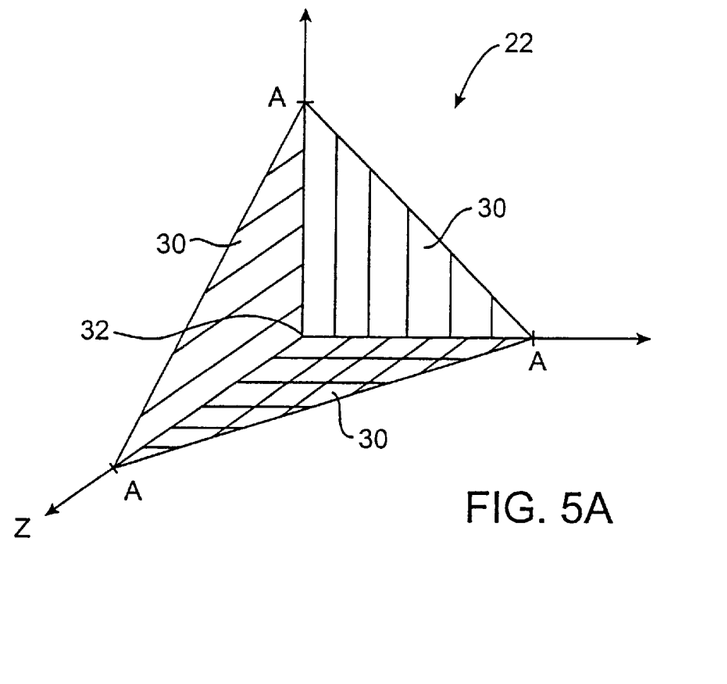
FIGS. 5A and 5B depict alternative configurations of corner reflectors for use with the present invention.
Figure 5B:
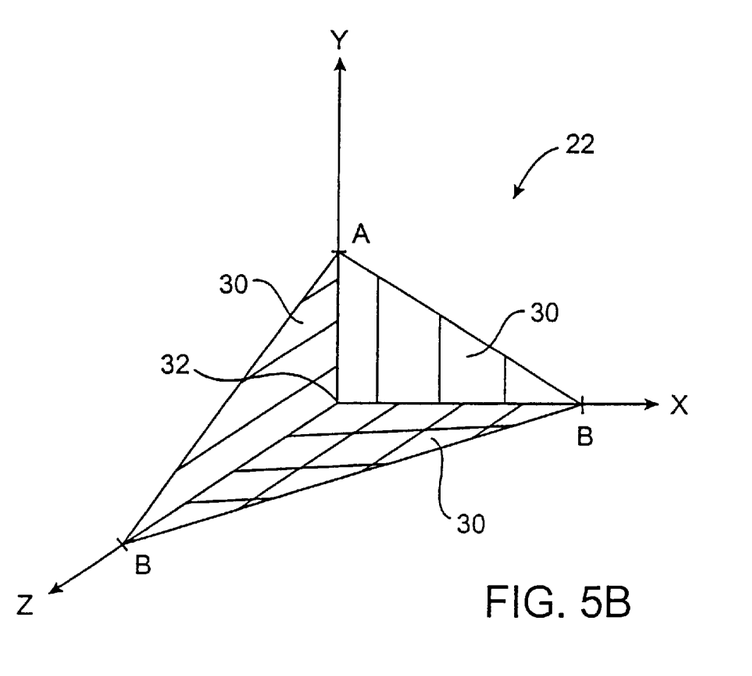
Figure 6A:
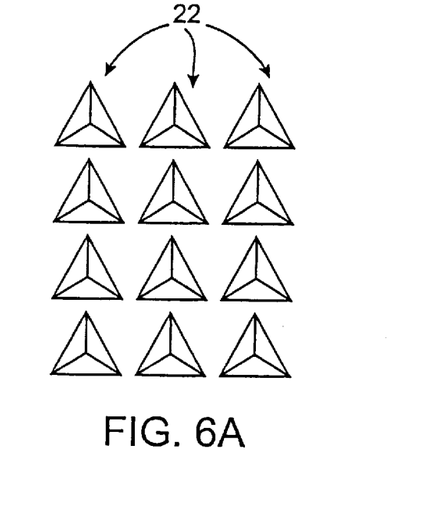
FIGS. 6A–6D depict alternative layouts of corner reflectors within an embossed portion according to the present invention.
Figure 6B:
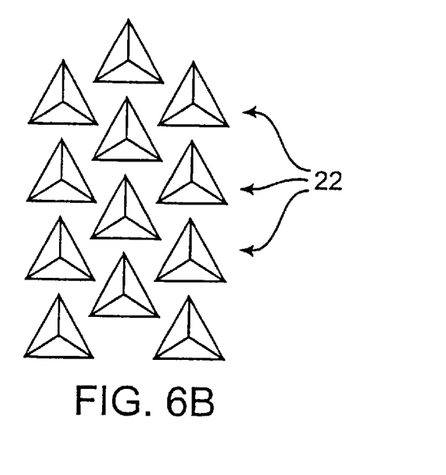
Figure 6C:
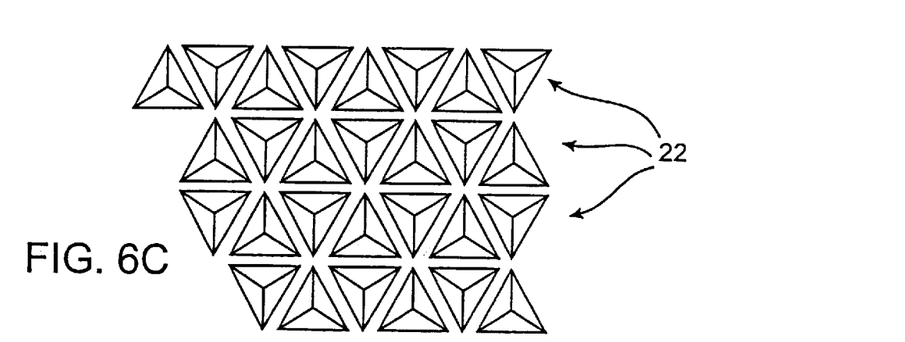
Figure 6D:
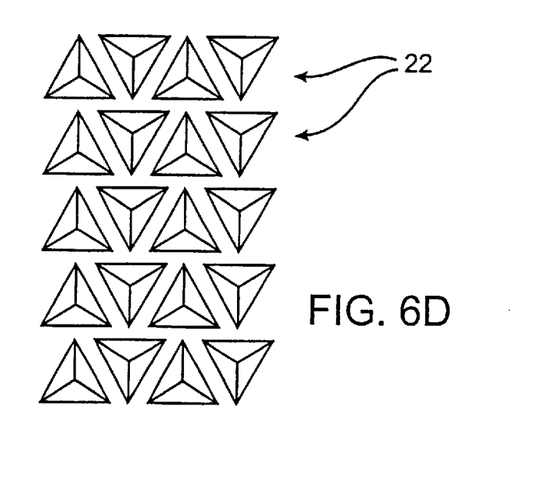

As shown in FIGS. 5A and 5B, corner reflectors 22 may have a variety of configurations. FIG. 5A depicts a three-sided corner reflector 22 having sides 30 connected to a common vertex 32. Each side 30 is positioned to be generally orthogonal to the other two sides and, for the embodiment shown in FIG. 5A, each side 30 has an isosceles triangle shape.

Similarly, corner reflector 22 depicted in FIG. 5B has three sides 30 sharing common vertex 32 whereby each side 30 has a right triangle shape. Again, each side 30 is generally orthogonal to the other two sides making up corner reflector 22.

FIGS. 6A–6D depict several alternative configurations of corner reflectors 22 to create embossed portion 20 within the scope of the present invention. It will be appreciated by those skilled in the art that notwithstanding the general symmetry of these three configurations, asymmetrical configurations of corner reflectors 22 also may be used within the scope of the present invention. Further, while FIGS. 6A–6D depict a field of corner reflectors 22 with small gaps or separations between adjacent corner reflectors 22 in the field, corner reflectors 22 also may share edges with some or all adjacent corner reflectors 22 thereto. This configuration enhances the amount of impinging energy that is reflected.

Figure 7:
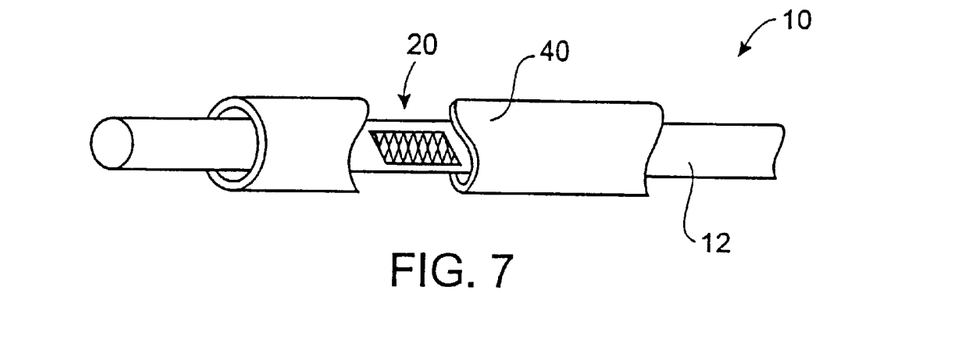
FIGS. 7–9 depict alternative embodiments of an apparatus of the present invention.

Turning now to FIG. 7, an exemplary embodiment of the present invention will be described. FIG. 7 depicts apparatus 10 as previously described in conjunction with FIGS. 1 and 2, comprising wire body 12 having embossed portion 20 of plurality of corner reflectors 22. Wire body 12 is disposed within a sleeve 40. It will be appreciated by those skilled in the art that sleeve 40 also may be used with the embodiments shown in FIGS. 3A–3F.

Sleeve 40 preferably comprises materials compatible with the introduction of apparatus 10 into a human patient. Sleeve 40 facilitates the introduction of wire body 12 within the patient, without embossed portion 20 being a frictional irritant to the inside walls of the patient vasculature. In one embodiment, sleeve 40 comprises one or more layers of plastic, polyethylene, and the like. Further, sleeve 40 preferably comprises materials that are generally transparent or minimally reflective to ultrasound energy, so that corner reflectors 22 on wire body 12 receive, and therefore reflect, the ultrasound signals.

Figure 8:
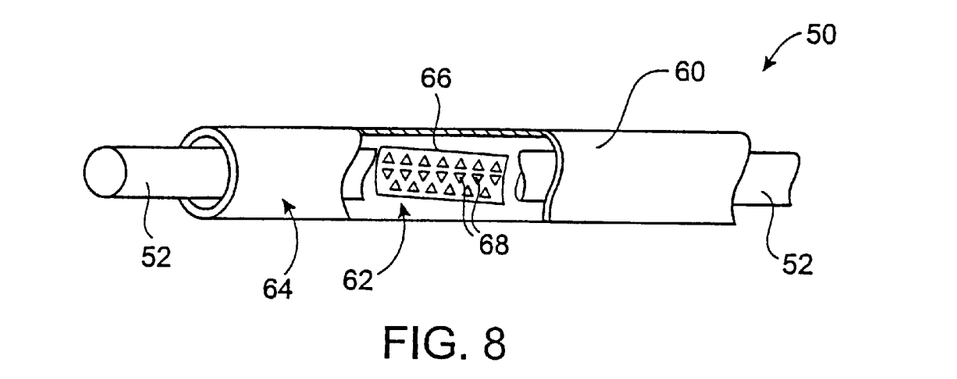
Figure 9:
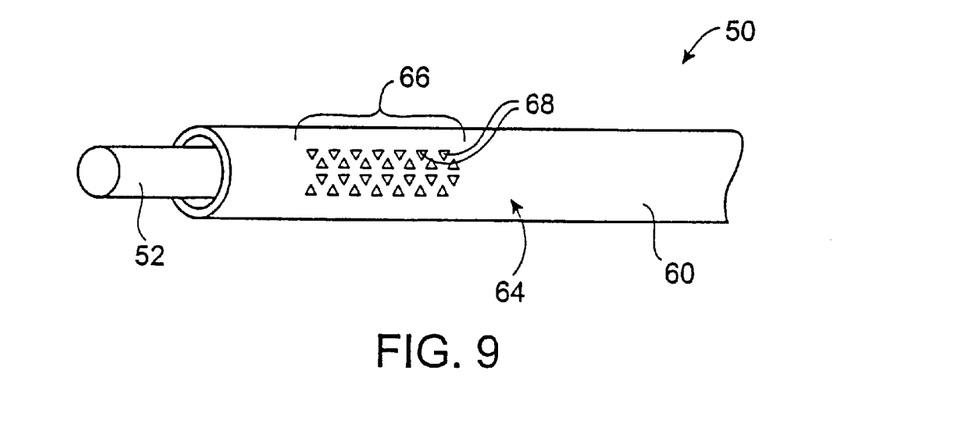

In an alternative embodiment, an apparatus 50 for use with invasive surgical procedures is shown in FIG. 8. Apparatus 50 includes a wire body 52, ostensibly as previously described with respect to size and materials, disposed within a sleeve 60. Sleeve 60 has an inner surface 62, an outer surface 64, and a plurality of corner reflectors 68 defining an embossed portion 66. In this manner, apparatus 50 includes wire body 52 disposed within sleeve 60, with embossed portion 66 disposed on inner surface 62 of sleeve 60. Alternatively, as shown in FIG. 9, embossed portion 66 is disposed on outer surface 64 of sleeve 60. In either configuration, plurality of corner reflectors 68 disposed on sleeve 60 facilitate the reflection of ultrasound signals from embossed portion 66, thereby increasing the visibility of apparatus 50. In the embodiments depicted in FIG. 8 and 9, some or all of sleeve 60 preferably comprises material selected from a group of materials consisting of a plastic, a metalized plastic, a metal, a plastic-coated metal, two or more plastics of different density, and the like. In this manner, embossed portion 66 is formed to be reflective of ultrasound energy, with corner reflectors 68 enhancing that reflectivity. Similarly, some or all of sleeve 60 may comprise a plastic, polyethylene and the like.

In one particular embodiment, embossed portion 68 is further coated with a material (not shown) having a density that is greater than a density of the materials making up sleeve 60. For example, a coating comprising chrome, tungsten, titanium and the like may be used. Ultrasound signals are reflected when the signals encounter a change in acoustic impedance that typically accompanies a change in density of the material through which the signals pass. In this manner, embossed portion 66 is more highly visible to ultrasound waves than the remaining portion of sleeve 60 due to corner reflectors 68 as previously described, and also due to the greater density material coating the corner reflectors having a greater acoustic impedance to reflect a greater percentage of the ultrasound signal.

In one embodiment, plastic corner reflectors 22 are metalized to improve reflectance or to optimize the density variation between sleeve layers. Such a configuration again takes advantage of the fact that ultrasound energy is reflected on changes in density of the material encountered. In one embodiment, corner reflectors 22 are coated with an impedance mismatching layer, such that the acoustic impedance of corner reflectors 22 differs from the surrounding sleeve material.

In another embodiment (not shown), multiple sleeves are used. Corner reflectors 22 are embossed on the outer surface of an inner sleeve. The inner sleeve is disposed in or integrally formed with an outer sleeve that is coated to provide a protective, smooth or lubricious surface, to facilitate introduction into a patient with reduced likelihood of irritating the body lumen or vessel walls.

While FIGS. 7–9 each depicted a single embossed portion 20 or 60 on apparatus 10 or 50, each apparatus could further include additional embossed portions. For example, wire body 12 in FIG. 7 may have a second embossed portion (not shown) located proximal of embossed portion 20. Apparatus 10 also may have second embossed portion (not shown) on sleeve 40 inner surface or outer surface. Apparatus 10, 50 having two embossed portions can be used in a variety of ways. By way of example and not limitation, sleeve 40-wire body 12 alignment can be achieved by aligning an embossed portion on sleeve 40 with embossed portion 20. Another use involves providing two locations on apparatus 10 with enhanced ultrasound reflective qualities. Similarly, apparatus 50 may have a second embossed portion on wire body 52 or sleeve 60.

Figure 10:
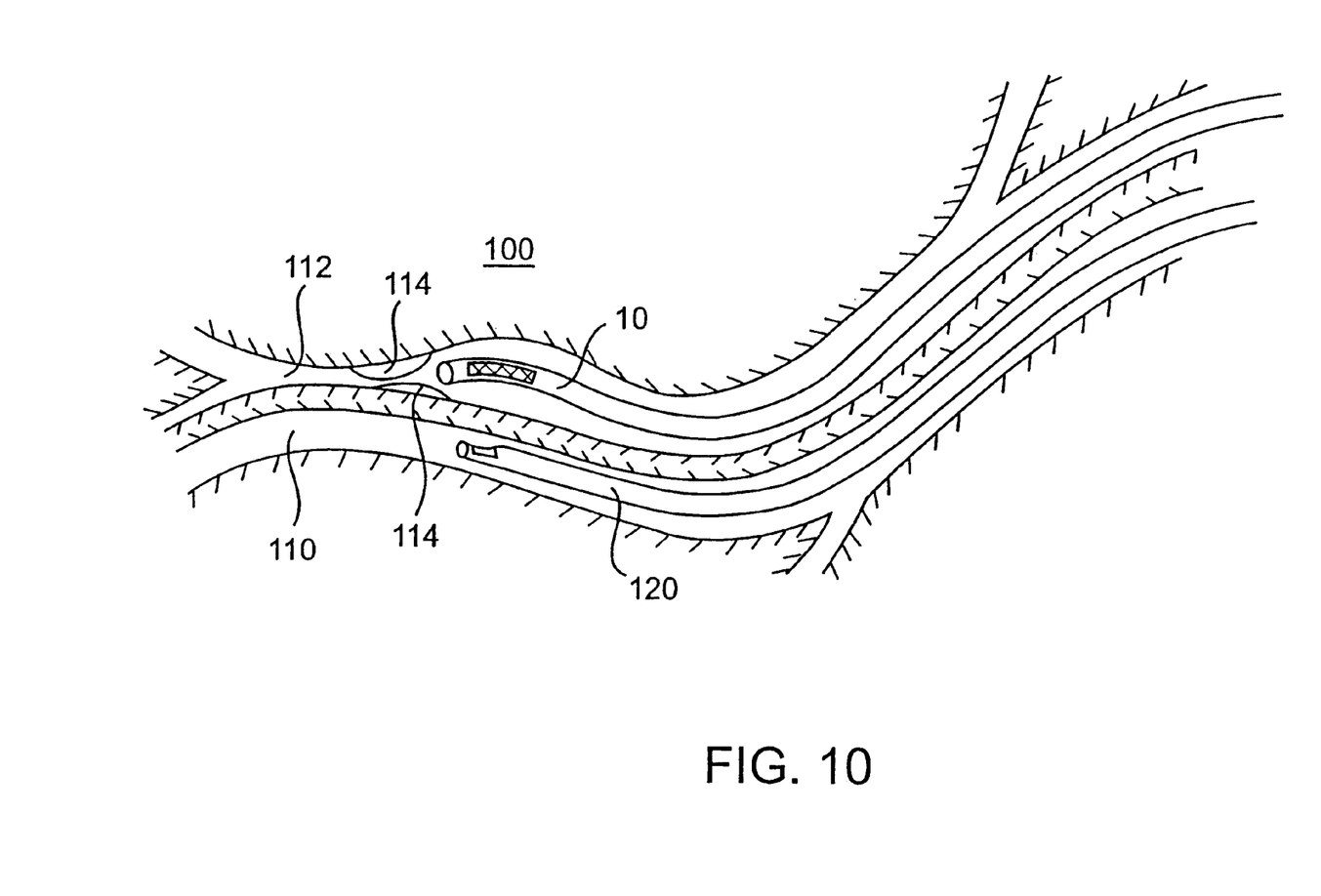
FIG. 10 depicts a lucent Are and ultrasound imaging catheter disposed within a patient in accordance with methods of the present invention.

Turning to FIG. 10, an exemplary method of using sonic lucent apparatus of the present invention will be described in conjunction with a less invasive surgical procedure. FIG. 10 depicts a patient 100 having a vein 110 and an artery 112. It will be appreciated by those skilled in the art that the method also applies with an artery 110 vein 112 combination, with two arteries or two veins. An occlusion 114 at least partially blocks a portion of artery 112. In this particular method, apparatus 10 is inserted into artery 112 up until the blockage or occlusion 114, which prevents further passage of apparatus 10. An imaging catheter 120, such as an ultrasound imaging catheter, is disposed within the adjacent vein 110. Alternatively, ultrasound imaging can occur from an ultrasound device maintained outside the patient. Imaging catheter 120 comprises a transducer element positioned at the distal end of catheter 120 which propagates ultrasound signals into the surrounding tissue and fluids. The ultrasound signal reflects off of tissue to transmit a reflected signal to the transducer. The reflected signal is translated by the transducer of the imaging catheter 120 into a video image of the tissue by techniques known to those skilled in the art.

Imaging catheter 120 is positioned within vein 110 in part by using the reflective nature of corner reflectors 22 on the embossed portion 20 of apparatus 10 to locate the distal end of wire body 12. In this manner, the general location of occlusion 114 can be more easily located by having a sonic lucent region made up of corner reflectors embossed on wire body 12. For the apparatus 10 shown in FIGS. 2A or 2C, having embossed portion 20 comprising only a portion of the outer surface of wire body 12, corner reflectors 22 can be positioned to face the transducer until the guidewire is located. Once the imaging catheter is properly positioned, the guidewire can be rotated to position corner reflectors 22 to be facing generally away from the imaging catheter to reduce the amount of the reflected signal.

It will be appreciated by those skilled in the art that the above description in conjunction with FIG. 10 represents but one of a large number of invasive imaging or surgical procedures for which the apparatus of the present invention may be used.

The invention has now been described in detail. However, it will be appreciated that certain changes and modifications may be made. For example, while described generally in conjunction with blood vessel treatments, apparatus and methods of the present invention may be used with a wide range of medical procedures. Virtually any invasive procedure with an instrument inserted into the body can benefit from the present invention to help precisely locate that instrument. Esophageal probes, for example, can either be embossed with corner reflectors 22 or used in conjunction with apparatus 10 or 50 of the present invention to enhance the visibility thereof to ultrasound or other energy wave. Further, the ultrasound source can be maintained outside the patient body, or be inserted inside the patient such as with an imaging catheter. Therefore, the scope and content of this invention are not limited by the foregoing description. Rather, the scope and content are to be defined by the following claims.

What is claimed is:

1. An apparatus to aid ultrasound imaging or treatment of a patient, comprising:
   an elongate wire body having an outer surface and a longitudinal axis;
   said wire body comprising a plurality of corner reflectors disposed on an embossed portion of said outer surface, said plurality of corner reflectors capable of reflecting ultrasound; and
   wherein said wire body is adapted to be inserted into a body lumen or a patient vasculature.

2. An apparatus as in claim 1, wherein said embossed portion is positioned to be generally coaxial with said longitudinal axis and extends around a portion of a circumference of said wire body.

3. An apparatus as in claim 1, wherein said embossed portion comprises a band around a circumference of said wire body.

4. An apparatus as in claim 1, wherein said wire body has a diameter that is less than about 20 French.

5. An apparatus as in claim 1, wherein said wire body comprises a stainless steel.

6. An apparatus as in claim 1, wherein said wire body comprises ningsten.

7. An apparatus as in claim 1, wherein each of said plurality of corner reflectors comprises first, second and third sides, each of said sides having a generally triangular shape and positioned to be generally orthogonal to the other two sides.

8. An apparatus as in claim 7, wherein each of said three sides have an isosceles triangle shape.

9. An apparatus as in claim 7, wherein each of said three sides have a right triangle shape and share a common vertex.

10. An apparatus as in claim 1, further comprising a sleeve, said wire body disposed within said sleeve.

11. An apparatus as in claim 10, wherein said sleeve comprises a material selected from a group of materials consisting of a plastic, a metal, a metal-coated plastic, a plastic-coated metal, and two or more plastics of different density.

12. An apparatus as in claim 1, further comprising a second embossed portion of said wire body embossed with a second plurality of corner reflectors.

13. An apparatus as in claim 1, wherein said wire body comprises a wound wire body.

14. An apparatus as in claim 13, wherein said wound wire body comprises a plurality of windings around said body longitudinal axis.

15. An ultrasound lucent wire, comprising:
   a wound wire body having a flexible distal end, a proximal end, a longidinal axis and an outer surface,
   said wire body comprising a plurality of corner reflectors embossed in said outer surface to define an embossed portion thereof, said plurality of corner reflectors adapted to reflect ultrasound,
   said wire body having a diameter that is less than about 20 French.

16. An apparatus to aid ultrasound imaging or treatment of a patient, comprising:
   a hollow sleeve having an inner surface and an outer surface; and
   a flexible wire disposed within said sleeve, wherein at least a portion of said wire is embossed with a plurality of corner reflectors, said plurality of corner reflectors adapted to reflect ultrasound.

17. An apparatus as in claim 16, wherein said flexible wire comprises a wound flexible wire.

18. An apparatus to aid ultrasound imaging or treatment of a patient, comprising:
   a hollow sleeve having an inner surface and an outer surface; and
   a flexible wire disposed in said sleeve;
   wherein said sleeve has a first portion embossed with a plurality of corner reflectors, said plurality of corner reflectors adapted to reflect ultrasound.

19. An apparatus as in claim 18, wherein said first sleeve portion comprises a portion of said inner surface.

20. An apparatus as in claim 18, wherein said first sleeve portion comprises a portion of said outer surface.

21. An apparatus as in claim 18, wherein said flexible wire comprises a wound flexible wire.

22. An apparatus as in claim 18, wherein said sleeve comprises a sleeve material having a sleeve material density, and said first sleeve portion is coated with a material having a greater density than a sleeve material density.

23. An apparatus as in claim 18, wherein each of said plurality of corner reflectors comprises first, second and third sides, each of said sides having a generally triangular shape and positioned to be generally orthogonal to the other two sides.

24. An apparatus as in claim 18, said sleeve further comprising a second embossed portion embossed with a second plurality of corner reflectors.

25. An apparatus as in claim 18, said wire comprising a wire outer surface at least partially embossed with a second plurality of corner reflectors.

26. An apparatus as in claim 18, further comprising a second sleeve into which said first sleeve is disposed.

27. A method of performing an invasive medical procedure comprising:
    providing a guide wire comprising
        a wire body having a flexible distal end, a proximal end, a longitudinal axis and an outer surface,
        said wire body comprising a plurality of corner reflectors embossed in said outer surface to define an embossed portion thereof,
    inserting said guide wire into a patient;
    positioning said guide wire at a desired location within said patient;
    energizing a transducer to project an ultrasound signal in the general direction of said embossed portion;
    capturing a reflected signal from said embossed portion; and
    rotating said guide wire so that said embossed portion faces away from said transducer.

28. The method of claim 27, further comprising inserting an ultrasound imaging catheter having said transducer into said patient.

29. An apparatus to aid ultrasound imaging or treatment of a patient, comprising:
    an elongate wire body having an outer surface and a longitudinal axis;
    said wire body comprising a plurality of corner reflectors disposed on an embossed portion of said outer surface, said plurality of corner reflectors adapted to reflect ultrasound; and
    wherein at least said wire body embossed portion is adapted to be inserted into a body lumen or a patient vasculature.

* * * * *